United States Patent
Sayre

(10) Patent No.: US 9,161,922 B2
(45) Date of Patent: Oct. 20, 2015

(54) AMINE OXIDASE INHIBITORS

(75) Inventor: Lawrence M. Sayre, Cleveland, OH (US)

(73) Assignee: Case Western Reserve University, Cleveland, OH (US)

(*) Notice: Subject to any disclaimer, the term of this patent is extended or adjusted under 35 U.S.C. 154(b) by 1519 days.

(21) Appl. No.: 11/994,017

(22) PCT Filed: Jun. 30, 2006

(86) PCT No.: PCT/US2006/025823
§ 371 (c)(1),
(2), (4) Date: Dec. 27, 2007

(87) PCT Pub. No.: WO2007/005737
PCT Pub. Date: Jan. 11, 2007

(65) Prior Publication Data
US 2008/0199933 A1 Aug. 21, 2008

Related U.S. Application Data

(60) Provisional application No. 60/695,950, filed on Jul. 1, 2005.

(51) Int. Cl.
*A61K 31/137* (2006.01)

(52) U.S. Cl.
CPC .................................. *A61K 31/137* (2013.01)

(58) Field of Classification Search
None
See application file for complete search history.

(56) References Cited

U.S. PATENT DOCUMENTS

| | | | |
|---|---|---|---|
| 4,088,668 A * | 5/1978 | Metcalf et al. | 549/214 |
| 4,537,902 A | 8/1985 | Cragoe et al. | |
| 4,851,447 A | 7/1989 | Bey | |
| 5,182,297 A | 1/1993 | Palfreyman et al. | |
| 2002/0038025 A1* | 3/2002 | Ackermann et al. | 544/332 |
| 2005/0096360 A1 | 5/2005 | Salter-Cid et al. | |

OTHER PUBLICATIONS

Dunkel et al. (Expert Opin. Ther. Patents, 21(9):1453-1471, 2011).*
Jeon, Heung-Bae, et al., "*Inactivation of bovine plasma amine oxidase by 4-aryloxy2butynamines and related analogs*", Biochimica et Biophysica Acta 1647 (2003 343-354.
Jeon, Heung-Bae, et al. "*Highly potent propargylamine and allylamine inhibitors of bovine plasma amine oxidase*", Biochemical and Biophysical Research Communication 304 (2003) 788-794.
Jeon, Heung-Bae, et al., "*Inhibition of Bovine Plasma Amine Oxidase by 1,4-Diamino-2-butenes and -2-butynes*", Bioorganic & Medicinal Chemistry 11 (2003) 4631-4641.
Lee, Younghee et al., "*3-Pyrrolines are Mechanism-Based Inactivators of the Quinone-Dependent Amine Oxidase but Only Substrates of the Flavin-Dependent Amine Oxidases*", J. Am. Chem. Soc. 2002, 124, 12135-12143.
O'Connell, Kimberly M., "*Differential Inhibition of Six Copper Amine Oxidases by a Family of 4-(Aryloxy)-2-butynamines: Evidence for a New Mode of Inactivation*", Biochemistry 2004, 43, 10965-10978.
Qiao, Chunhua, et al., "*Selective Inhibition of Bovine Plasma Amine Oxidase by Homoproparglamine, a New Inactivator Motif*", J. Am. Chem. Soc. 2004, 126, 8038-8045.
Shepard, et al. Towards the development of selective amine oxidase inhibitors—Mechanism based inhibition of six copper containing amine oxidases; Eur. J. Biochem., May 31, 2002, vol. 269, p. 3645-3658, entire document.

* cited by examiner

*Primary Examiner* — Bong-Sook Baek
(74) *Attorney, Agent, or Firm* — Tarolli, Sundheim, Covell & Tummino LLP

(57) ABSTRACT

A therapeutic agent for selectively inhibiting amine oxidases associated diseases and conditions in humans includes at least one compound selected from the group consisting of propargylamines, polypropargylamines, homopropargylamines, 4-substituted-2-butynylamines, 2- and 3-halloallylamines, pyrroline derivatives, cycloalkenyl branched primary amines, propargyl diamines, homopropargyl amines and diamines, allenyl amines and diamines, chloroallyl diamines, lysyne analogs, β-haloamines, RF-substituted amines, RCi-substituted amines, and R3Si substituted amines.

1 Claim, No Drawings

AMINE OXIDASE INHIBITORS

RELATED APPLICATION

This application corresponds to PCT/US06/25823, filed Jun. 30, 2006, which claims priority from U.S. Provisional Application No. 60/695,950, filed Jul. 1, 2005, which is herein incorporated by reference it its entirety.

GOVERNMENT RIGHTS

The invention described in this application was supported, at least in part, by United Stated Government Grant No. NIH Grant No. GM48812 with the National Institutes of Health.

TECHNICAL FIELD

The present application relates to copper amine oxidase inhibitors and to methods of using such inhibitors for therapeutic applications.

BACKGROUND

There are now known to be three human genes that code for the TPQ-containing amine oxidases, AOC1, AOC2, and AOC3.

AOC1 is the diamine oxidase found primarily in kidney (HKDAO), though it is also expressed in the liver and brain. The enzyme is thought to be involved in the catabolism of histamine and of putrescine and other polyamines, important mediators of nuclear events underlying cell proliferation. This suggests a fundamental role of HKDAO in the regulation of growth. At the same time, the $H_2O_2$ and aldehydes resulting from polyamine metabolism have been suggested to contribute to apoptotic cell death in brain injury. The presence of DAO at the interface between rapidly dividing (e.g., epithelial) and quiescent cells suggests that it might be involved in regulating cell division or differentiation at tissue boundaries. Involvement of DAO in the metabolism of histamine implicates its role in the progression of inflammation.

AOC2 is the retina-specific amine oxidase. The function is not yet clear, and there have been no suggestions in the prior art of a possible therapeutic effect of having a specific inhibitor of this enzyme.

AOC3 codes for an amine oxidase, which is also the human vascular adhesion protein (HVAP-1), responsible for the binding of lymphocytes to the endothelial cell surface and the promotion of their transendothelial migration. A number of studies point to this enzyme being a useful anti-inflammatory target. Further, since leukocyte migration from the blood to tissues is a prerequisite for normal immune responses, inhibitors of HVAP-1 will be important for modulating the immune response. This enzyme, responsible for the semicarbazide-sensitive amine oxidase (SSAO) activity in mammalian tissues, is largely associated with the plasma membrane of various tissues, and is particularly high in vascular and nonvascular smooth muscle cells, but is also found in other cell types such as adipocytes, chondrocytes, and odontoblasts. There are several pathological states where increased circulating SSAO activity has been found: diabetes mellitus, congestive heart failure, cerebral infarction, uremia, inflammatory liver diseases (e.g., cirrhosis), obesity, and hyperlipidemia. High levels of SSAO are also found in atherosclerotic plaques, and serum SSAO activity correlates with the severity of atherosclerosis, as well as intima-media thickness and serum cholesterol levels. It has been proposed that vascular SSAO is involved in the regulation of vascular tone, and thus vascular SSAO inhibition may offer a novel mechanism of vasodilation.

The role of SSAO in the pathophysiology of diabetes has been most extensively investigated. Elevated SSAO activity is associated with type 1 diabetes already at first clinical diagnosis, and in type 2 diabetes, particularly in diabetic patients with vascular complications, such as retinopathy and arteriosclerosis. It has therefore been speculated that SSAO may contribute to the development of vascular complications associated with diabetes. SSAO is associated with translocation of the glucose transporter GLUT4 into the adipose cell surface and thereby promotes glucose uptake in adipose tissue and smooth muscle cells. SSAO contributes to elevated formation of cytotoxic metabolites (principally methylglyoxal from aminoacetone, formaldehyde from methylamine, and $H_2O_2$ as by-product) that exacerbate advanced glycation of proteins (including crosslinking) and cause endothelial injury of blood vessels, resulting in early development of atherosclerosis and late-stage diabetic complications such as neuropathy, retinopathy, and nepropathy. Thus SSAO inhibitors may be ameliorative in the development of atherosclerosis and diabetic complications. Plasma SSAO activity is elevated in morbidly obese patients, which might contribute to the increased cardiovascular risk associated with obesity. A potent, selective SSAO inhibitor was found to reduce atherogenesis in a genetically obese diabetic mouse strain fed a high cholesterol diet. Furthermore, a recent study showed that an antibody to block VAP-1 in mice prevented diabetes in a subset of nonobese diabetic mice. Interestingly, aminoguanidine, which blocks advanced glycation and reduces nephropathy in animals, is more potent at inhibiting SSAO than its affect on glycation.

In addition to the LTQ-containing lysyl oxidase (LOX), human genes for four LOX-like proteins have been recently identified: LOXL, LOXL2, LOXL3 and LOXL4. In most tissues, LOX is responsible for the lysine-derived cross-links in collagen and elastin, which is the essential step for biogenesis and repair of the fibrillar extracellular matrix. Despite what should be a harmful effect of lysyl oxidase inhibition early in life, there is growing evidence that the enzyme also plays a role in late-onset fibrotic conditions in man.

SUMMARY

The present invention relates to a method of inhibiting quinone-dependent copper amine oxidases. In the method, the quinone dependent copper amine oxidase is contacted with an inhibitory amount of a compound selected from the group consisting of propargylamines, such as simple propargylamines, and double or triple bond conjugated propargylamines, trialkylsilyl substituted propargylamines, polypropargylamines, homopropargylamines, 4-substituted-2-butynylamines, 2- and 3-halloallylamines, such as 3-chloroallylamines, 3-(alkoxycarbonyl)-3-chloroallylamines, 2- and 3-aryl-3-haloallylamines, 2-halo-3-arylallylamines, 3-halo-2-methylallylamines, 2-haloallylamines, pyrroline derivatives, cycloalkenyl branched primary amines, propargyl diamines, homopropargyl amines and diamines, allenyl amines and diamines, chloroallyl diamines, lysyne analogues, referring to a propargylamine inside a lysine side-chain, β-haloamines, $R_F$-substituted amines, $R_{Cl}$-substituted amines, and $R_3Si$ substituted amines.

In an aspect of the invention, the compounds can be used as selective inhibitors of amine oxidases, such as human TPQ-containing amine oxidases (e.g., AOC1, AOC2, AOC3, and SSAO), human LTQ-containing amine oxidases (e.g., LOX, LOXL, LOXL2, LOX3, and LOXL4), as well as other human copper amine oxidases and non-mammalian copper amine oxidases.

In another aspect of the invention, the compounds can be used as therapeutic agents for treating a number of inflammatory conditions and diseases of connective tissue, skin, and the gastrointestinal, central nervous system, and pulmonary systems, including such conditions as chronic arthritis, inflammatory bowel diseases, and chronic dermatoses. The therapeutic agents can also be useful for treating diseases related to carbohydrate metabolism (such as diabetes), to aberrations in adipocyte differentiation or function or smooth muscle cell function (such as atherosclerosis and obesity), and to various vascular diseases (such as atheromatous and nonatheromatous arteriosclerosis, ischemic heart disease, and peripheral arterial occlusion). The therapeutic agent can further be used for anti-fibrotic chemotherapies, tumor suppression, cellular senescence, developmental control, cell motility (chemotaxis), hepatic fibrosis, Alzheimer's disease, anti-bacterial, anti-microbial, and anti-fungal agents.

A further aspect of the present invention is to provide a pharmaceutical composition useful for treating disorders responsive to an increase in amine oxidase activity, containing an effective amount of the therapeutic agent in a mixture with one or more pharmaceutically acceptable carriers or diluents.

DETAILED DESCRIPTION

The present invention relates to compounds or therapeutic agents that can be used as selective inhibitors of quinone dependent copper amine oxidases, such as mammalian (e.g., human) trihydroxyphenylalanine quinone (TPQ)-containing amine oxidases (e.g., AOC1, AOC2, AOC3, and SSAO), LTQ-containing amine oxidases (e.g., LOX, LOXL, LOXL2, LOX3, and LOXL4), as well as other mammalian copper amine oxidases and non-mammalian copper amine oxidases.

In an aspect of the invention, the therapeutic agent can comprise a propargylamine with the following general formula (I):

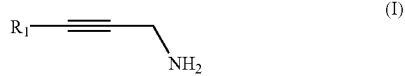

(I)

where $R_1$ represents substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$, aryl, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, substituted aryl, substituted alkyl, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

The phrase "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocyclohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary alkyl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted aryl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ alkylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_1$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(alkyl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

When referring to a compound of the invention, applicants intend the term "compound" to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

Some of the compounds disclosed herein may contain one or more asymmetric centers and may thus give rise to enantiomers, diastereomers, and other stereoisomeric forms. The present invention is also meant to encompass racemic mixtures, resolved forms and mixtures thereof, as well as the individual enantiomers that may be separated according to methods that are well know to those of ordinary skill in the art. When the compounds described herein contain olefinic double bonds or other centers of geometric asymmetry, and unless specified otherwise, it is intended to include both E and Z geometric isomers.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "asymmetric center" or "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its minor image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

In one subclass of propargylamines, the therapeutic agent can be a simple propargylamine. Examples of simple propargylamines can include:

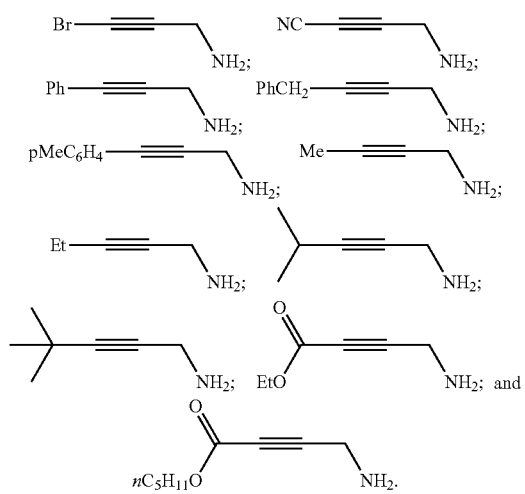

In another subclass of propargylamines, the therapeutic agent can be a triple bond conjugated propargylamine. Examples of triple bond conjugated propargylamines can include:

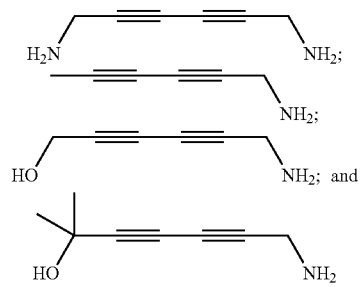

In a further subclass propargylamines, the therapeutic agent can be a triaklylsilyl substituted propargylamines. Trialkylsilyl substituted propargylamines can act as potential prodrugs. The acetylenyl-Si bond can hydrolyze to release propargylamine or conjugated propargylamine. Examples of trialkylsilyl substituted propargylamines can include:

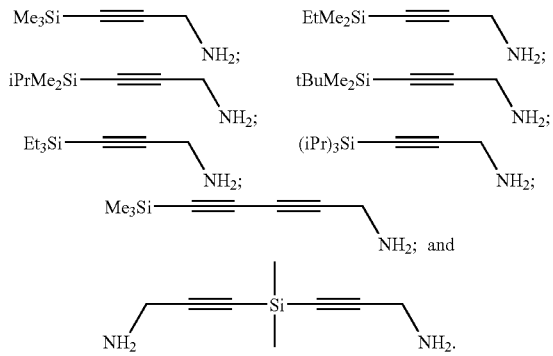

In accordance with another aspect, the therapeutic agent can comprise a polypropargylamine with the following general formula (II):

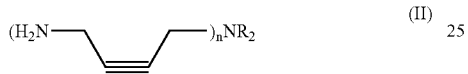

where n=1, 2, or 3, and $R_2$ is selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, substituted aryl, substituted alkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof, or a pharmaceutically acceptable salt thereof.

In a subclass of polypropargylamines, n=1, 2, or 3 and $R_2$ is selected from the group consisting of H, CH$_3$, and PhCH$_2$. Examples of polypropargylamines of this subclass can include:

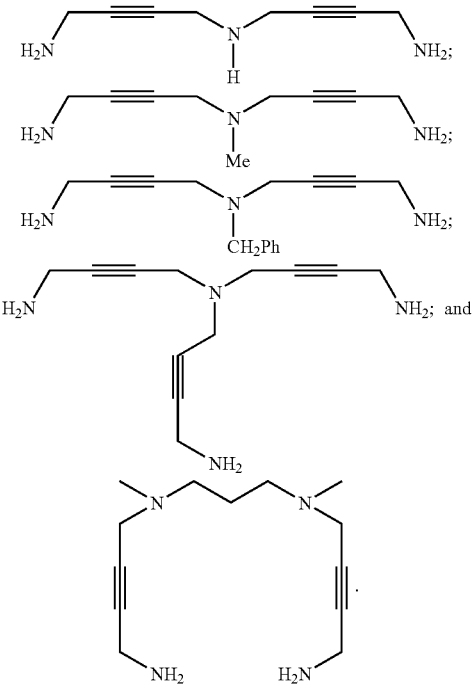

In accordance with a further aspect, the therapeutic agent can comprise a homopropargylamine with the following general formula (III):

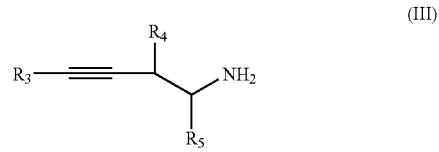

where $R_3$, $R_4$, and $R_5$ can each be individually selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, substituted aryl, substituted alkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—N—H$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR═N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

In a subclass of homopropargylamines, R$_3$ can be selected from the group consisting of H, alkyl, aryl, halo, and cyano, and R$_4$ and R$_5$ can be each be independently selected from the group consisting of H, alkyl, and aryl. Examples of homopropargylamines of this subclass can include:

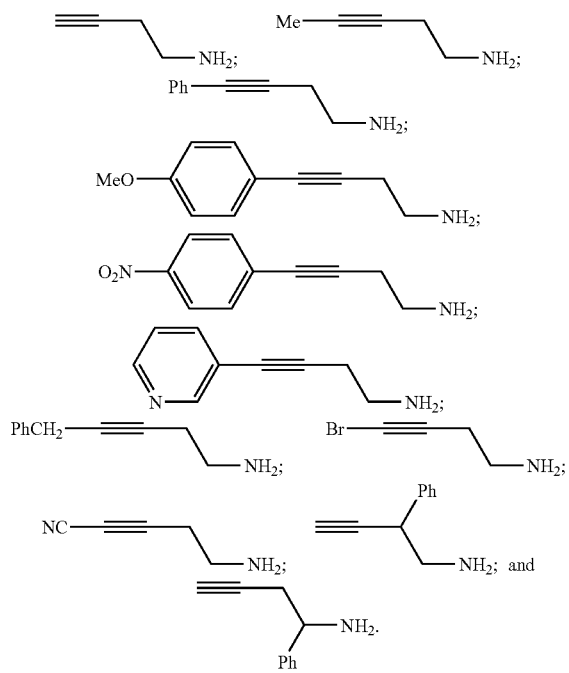

In accordance with a further aspect, the therapeutic agent can comprise a 4-R$_6$X$_1$-substituted 2-butynylamine with the following general formula (IV):

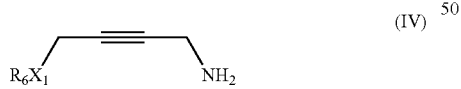

(IV)

where X$_1$ is selected from the group consisting of O, S, and C(═O)NH, and where R$_6$ is selected from the group consisting of hydrogen, C$_1$-C$_{24}$ alkyl, C$_2$-C$_{24}$ alkenyl, C$_2$-C$_{24}$ alkynyl, C$_3$-C$_{20}$ aryl, C$_6$-C$_{24}$ alkaryl, C$_6$-C$_{24}$ aralkyl, substituted aryl, substituted alkyl, halo, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl-(—CO-aryl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$C$^-$), isothiocyanato (—S—CN), azido (—N═N$^+$═N$^-$), formyl (—(CO)—H), thioformyl (—(CS)—H), amino (—NH$_2$), mono- and di-(C$_1$-C$_{24}$ alkyl)-substituted amino, mono- and di-(C$_5$-C$_{20}$ aryl)-substituted amino, C$_2$-C$_{24}$ alkylamido (—NH—(CO)-alkyl), C$_6$-C$_{20}$ arylamido (—NH—(CO)-aryl), imino (—CR═NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR═N(alkyl), where R=hydrogen, alkyl, aryl, alkaryl, aralkyl, etc.), arylimino (—CR═N(aryl), where R=hydrogen, alkyl, aryl, alkaryl, etc.), nitro (—NO$_2$), nitroso (—NO), sulfo (—SO$_2$—OH), sulfonato (—SO$_2$—O, C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_1$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

In a subclass of 4-R$_6$X$_1$-substituted 2-butynylamine, R$_6$ can be selected from the group consisting of H, alkyl, and aryl, and X$_1$ can be selected from the group consisting of O and S. Examples of 4-R$_6$X$_1$-substituted 2-butynylamine of this subclass can include:

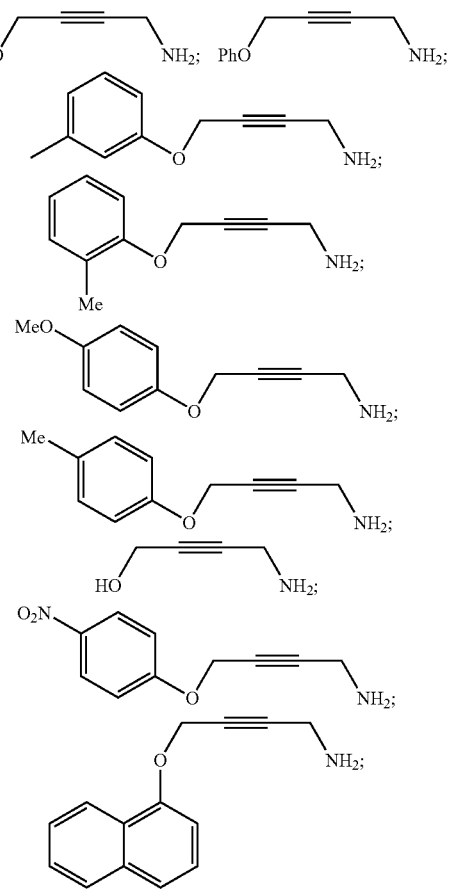

-continued

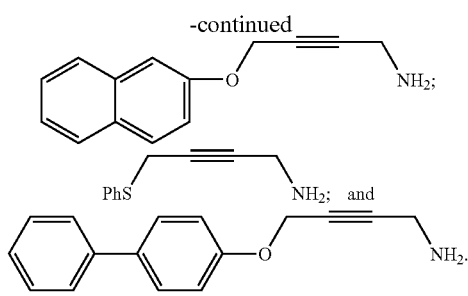

In another subclass of 4-R$_6$X$_1$-substituted 2-butynylamines, X$_1$ can be C(=O)NH. Examples of 4-R$_6$X$_1$-substituted 2-butynylamine of this subclass can include:

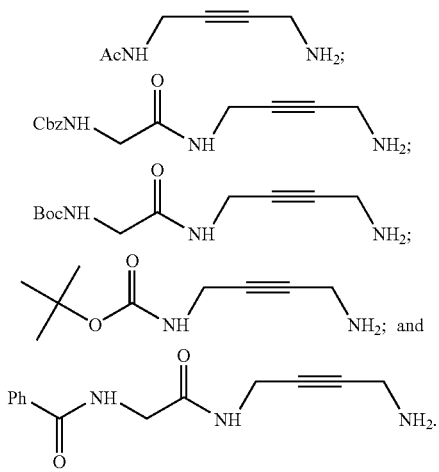

In accordance with yet another aspect, the therapeutic agent can comprise a 2- and 3-substituted halloallylamines with the following general formula (V):

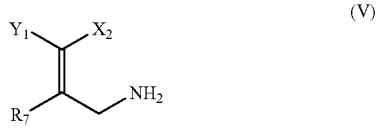
(V)

where R$_7$, Y$_1$, and X$_2$ can each be individually selected from the group consisting of hydrogen, C$_1$-C$_{24}$ alkyl, C$_2$-C$_{24}$ alkenyl, C$_2$-C$_{24}$ alkynyl, C$_3$-C$_{20}$ aryl, C$_6$-C$_{24}$ alkaryl, C$_6$-C$_{24}$ aralkyl, substituted aryl, substituted alkyl, halo, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-alkyl)), acyloxy (—O-acyl), C$_2$-C$_{24}$ alkoxycarbonyl (—(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$C$^-$), isothiocyanato (—S—CN), azido (—N=N$^+$=N$^-$), formyl (—(CO)—H), thioformyl (—(CS)—H), amino (—NH$_2$), mono- and di-(C$_1$-C$_{24}$ alkyl)-substituted amino, mono- and di-(C$_5$-C$_{20}$ aryl)-substituted amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof; or a pharmaceutically acceptable salt thereof.

In a subclass of 2- and 3-substituted halloallylamine, the therapeutic agent can be a simple 3-chloroallylamine. Examples of 3-chloroallylamines of this subclass can include:

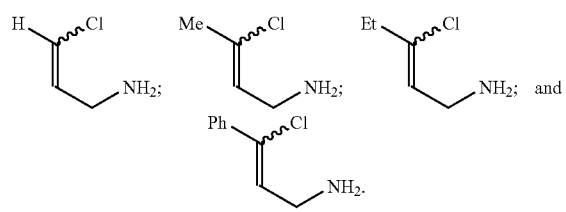

In another subclass of 2- and 3-substituted halloallylamines, the therapeutic agent can be 3-(alkoxycarbonyl)-3-chloroallylamines. Examples of 3-chloroallylamines of this subclass can include:

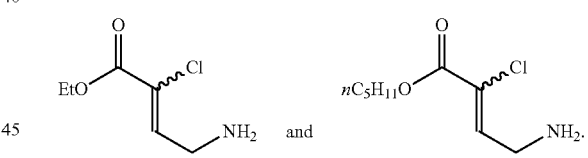

In further subclass of 2- and 3-substituted halloallylamines, the therapeutic agent can be a 2-phenyl-3-haloallylamine. Examples of 2-phenyl-3-haloallylamines of this subclass can include:

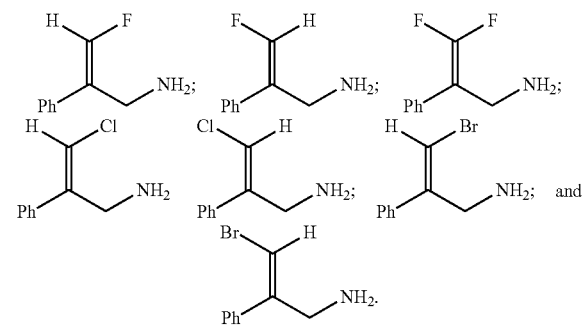

In yet a further subclass of 2- and 3-substituted halloallylamines, the therapeutic agent can be a 3-bromo-2-methylallylamine. Examples of 3-bromo-2-methylallylamines of this subclass can include:

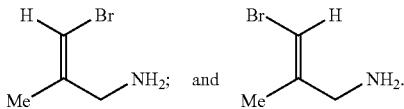 [SMILES: C/C(=C/Br)CN ; C/C(=C\Br)CN]

In another subclass of 2- and 3-substituted halloallylamine, the therapeutic agent can be a 2-chloroallylamine. Examples of 2-chloroallylamines of this subclass can include:

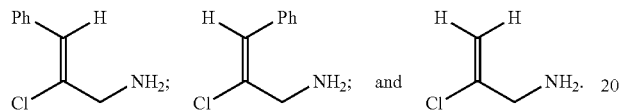

In accordance with yet another aspect, the therapeutic agent can comprise an allenyl amine with the following general formula (VI):

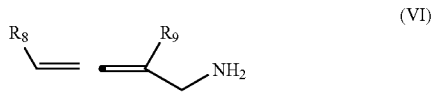

where $R_8$ and $R_9$ can each be individually selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, substituted aryl, substituted alkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N (alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)$_2$), phospho (—PO$_2$), phosphino (—PH$_2$), and combinations thereof; or a pharmaceutically acceptable salt thereof.

In a subclass of allenyl amines, $R_8$ can be selected from the group consisting of H, alkyl, and aryl, and $X_3$ substituted alkyl ($X_3$=O or N) and $R_9$ can be selected from the group consisting of H, alkyl, and aryl. Examples of allenyl amines of this subclass can include:

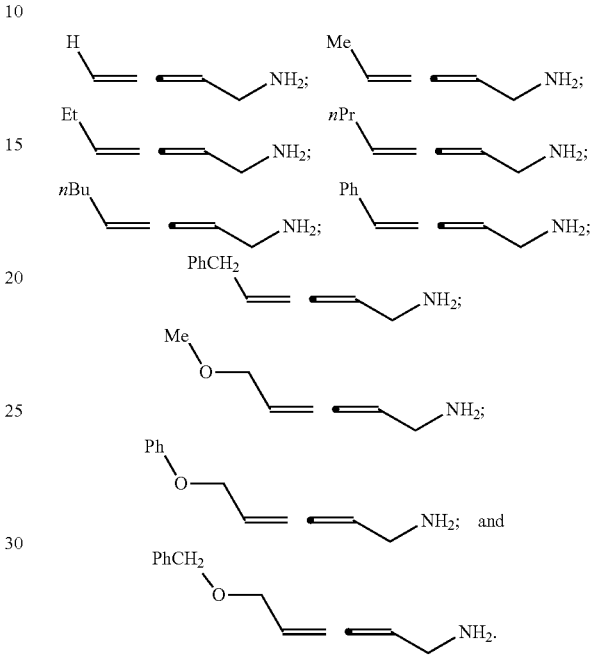

In accordance with yet another aspect, the therapeutic agent can comprise a pyrroline derivative with the following general formula (VII):

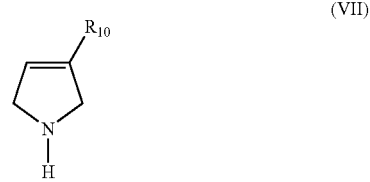

where $R_{10}$ can be selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, substituted aryl, substituted alkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$C$^-$), isothiocyanato (—S—CN), azido (—N=N+=N−), formyl (—(CO)—H), thioformyl (—(CS)—H), amino (—NH₂), mono- and di-($C_1$-$C_{24}$ alkyl)-substituted amino, mono- and di-($C_5$-$C_{20}$ alkyl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O−), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO₂-alkyl), $C_5$-$C_{20}$ arylsulfonyl (—SO₂-aryl), phosphono (—P(O)(OH)₂), phosphonato (—P(O)(O−)₂), phosphinato (—P(O)(O−)), phospho (—PO₂), phosphino (—PH₂), substituted aryl and combinations thereof; or a pharmaceutically acceptable salt thereof.

In a subclass of pyrroline derivatives, $R_{10}$ can be an aryl or heterocyclic aryl. Examples of pyrolline of this subclass can include:

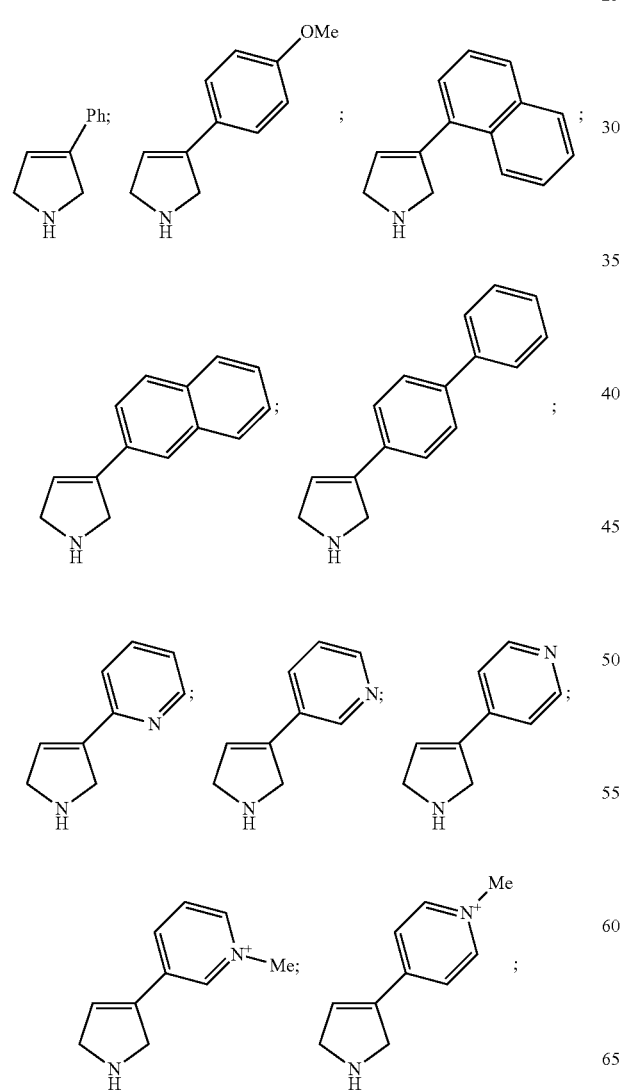

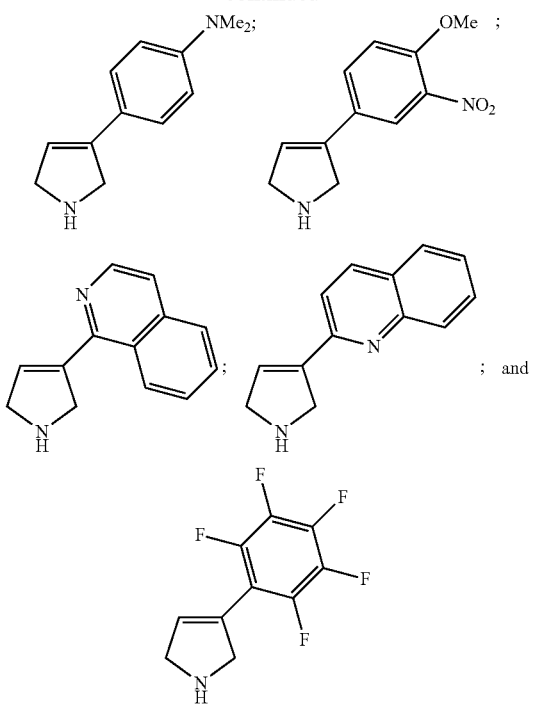

In accordance with yet a further aspect, the therapeutic agent can comprise a chlorinated homoallylamine, such as:

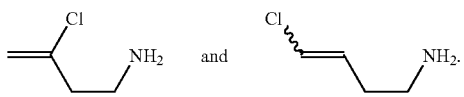

In accordance with another aspect, the therapeutic agent can comprise a cycloalkenyl branched primary amine, such as:

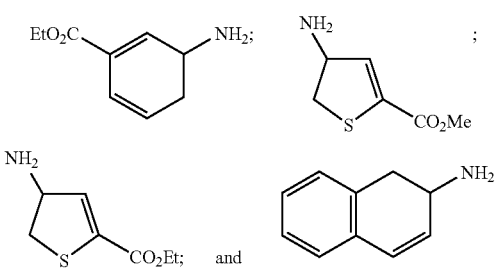

In accordance with yet another aspect, the therapeutic agent can comprise a diamine with the following general formula (VIII) or (IX).

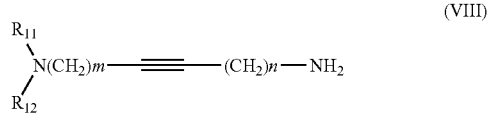

(VIII)

$$R_{13}\diagdown N(CH_2)m\text{—}\overset{X_4}{\equiv}\text{—}(CH_2)n\text{—}NH_2 \quad (IX)$$
$$R_{14}\diagup$$

where m and n are each independently 1 or 2, $X_4$ is a halo selected from the group consisting of Cl, Br, I, and F, and $R_1$, $R_{12}$, $R_{13}$, and $R_{14}$ are each independently selected from group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, substituted aryl, substituted alkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)₂), mono-substituted arylcarbamoyl (—(CO)—NH-aryl), thiocarbamoyl (—(CS)—NH₂), carbamido (—NH—(CO)—NH₂), cyano (—CN), isocyano (—N⁺C⁻), cyanato (—O—CN), isocyanato (—O—N⁺C⁻), isothiocyanato (—S—CN), azido (—N=N⁺=N⁻), formyl (—(CO)—H), thioformyl (—(CS)—H), amino (—NH₂), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO₂-alkyl), $C_5$-$C_{20}$ arylsulfonyl (—SO₂-aryl), phosphono (—P(O)(OH)₂), phosphonato (—P(O)(O⁻)₂), phosphinato (—P(O)(O⁻)), phospho (—PO₂), phosphino (—PH₂), and combinations thereof; or a pharmaceutically acceptable salt thereof.

In a subclass of diamines, the therapeutic agent can be a propargyl, homopropargyl, allenyl, or chlorovinyl, such as where $R_{11}$ and $R_{12}$ are each independently selected from the group consisting of Ph, Bz, PhCH₂CH₂, Me, and H, and $R_{13}$ and $R_{14}$ are each independently selected from group consisting of Me and H. Examples of diamines of this subclass can include:

In accordance with yet another aspect, the therapeutic agent can comprise a lysyne analogue with the following general formula:

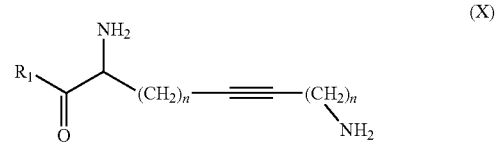

where n is 1 or 2 and $R_1$ is selected from group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, substituted aryl, substituted alkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)₂), mono-substituted arylcarbamoyl (—(CO)—NH-aryl), thiocarbamoyl (—(CS)—NH₂), carbamido (—NH—(CO)—N—H₂), cyano (—CN), isocyano (—N⁺C⁻), cyanato (—O—CN), isocyanato (—O—N⁺C⁻), isothiocyanato (—S—CN), azido (—N=N⁺=N⁻), formyl (—(CO)—H), thioformyl (—(CS)—H), amino (—N—H₂), mono- and di-(C₁-C₂₄ alkyl)-substituted amino, mono- and di-(C₅-C₂₀ aryl)-substituted amino, C₂-C₂₄ alkylamido (—NH—(CO)-alkyl), C₆-C₂₀ arylamido (—NH—(CO)-aryl), imino (—CR=NH where R is hydrogen, C₁-C₂₄ alkyl, C₅-C₂₀ aryl, C₆-C₂₄ alkaryl, C₆-C₂₄ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O⁻), C₁-C₂₄ alkylsulfanyl (—S-alkyl; also termed "alkylthio"), arylsulfanyl (—S-aryl; also termed "arylthio"), C₁-C₂₄ alkylsulfinyl (—(SO)-alkyl), C₅-C₂₀ arylsulfinyl (—(SO)-aryl), C₁-C₂₄ alkylsulfonyl (—SO₂-alkyl), C₅-C₂₀ arylsulfonyl (—SO₂-aryl), phosphono (—P(O)(OH)₂), phosphonato (—P(O)(O⁻)₂), phosphinato (—P(O)(O⁻)), phospho (—PO₂), phosphino (—PH₂), and combinations thereof; or a pharmaceutically acceptable salt thereof.

In subclass of lysyne analogues, the therapeutic agent can have the following general formula:

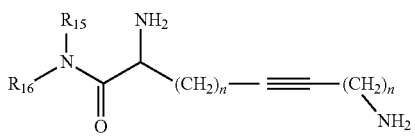

where n is 1 or 2 and R₁₅ and R₁₆ are each independently selected from group consisting of hydrogen, C₁-C₂₄ alkyl, C₂-C₂₄ alkenyl, C₂-C₂₄ alkynyl, C₃-C₂₀ aryl, C₆-C₂₄ alkaryl, C₆-C₂₄ aralkyl, substituted aryl, substituted alkyl, halo, hydroxyl, sulfhydryl, C₁-C₂₄ alkoxy, C₂-C₂₄ alkenyloxy, C₂-C₂₄ alkynyloxy, C₅-C₂₀ aryloxy, acyl (including C₂-C₂₄ alkylcarbonyl (—CO-alkyl) and CO—C₂₀ arylcarbonyl (—CO-aryl)), acyloxy (—O-acyl), C₂-C₂₄ alkoxycarbonyl (—(CO)—O-alkyl), C₆-C₂₀ aryloxycarbonyl (—(CO)—O-aryl), C₂-C₂₄ alkylcarbonato (—O—(CO)—O-alkyl), C₆-C₂₀ arylcarbonato (—O—(CO)—O-aryl), carboxy (—COOH), carboxylato (—COO⁻), carbamoyl (—(CO)—NH₂), mono-(C₁-C₂₄ alkyl)-substituted carbamoyl (—(CO)—NH(C₁-C₂₄ alkyl)), di-(C₁-C₂₄ alkyl)-substituted carbamoyl (—(CO)—N(C₁-C₂₄ alkyl)₂), mono-substituted arylcarbamoyl (—(CO)—NH-aryl), thiocarbamoyl (—(CS)—NH₂), carbamido (—NH—(CO)—NH₂), cyano (—CN), isocyano (—N⁺C), cyanato (—O—CN), isocyanato (—O—NC⁻), isothiocyanato (—S—CN), azido (—N=N⁺=N⁻), formyl (—(CO)—H), thioformyl (—(CS)—H), amino (—NH₂), mono- and di-(C₁-C₂₄ alkyl)-substituted amino, mono- and di-(C₅-C₂₀ aryl)-substituted amino, C₂-C₂₄ alkylamido (—NH—(CO)-alkyl), C₆-C₂₀ arylamido (—NH—(CO)-aryl), imino (—CR=NH where R is hydrogen, C₁-C₂₄ alkyl, C₅-C₂₀ aryl, C₆-C₂₄ alkaryl, C₆-C₂₄ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O⁻), C₁-C₂₄ alkylsulfanyl (—S-alkyl; also termed "alkylthio"), arylsulfanyl (—S-aryl; also termed "arylthio"), C₁-C₂₄ alkylsulfinyl (—(SO)-alkyl), C₅-C₂₀ arylsulfinyl (—(SO)-aryl), C₁-C₂₄ alkylsulfonyl (—SO₂-alkyl), C₅-C₂₀ arylsulfonyl (—SO₂-aryl), phosphono (—P(O)(OH)₂), phosphonato (—P(O)(O⁻)₂), phosphinato (—P(O)(O⁻)), phospho (—PO₂), phosphino (—PH₂), and combinations thereof, or a pharmaceutically acceptable salt thereof.

In a subclass of lysyne analogues, R₁₅ and R₁₆ can each be independently selected from group consisting of H, alkyl, and substituted alkyls. Examples of lysyne of this subclass can include:

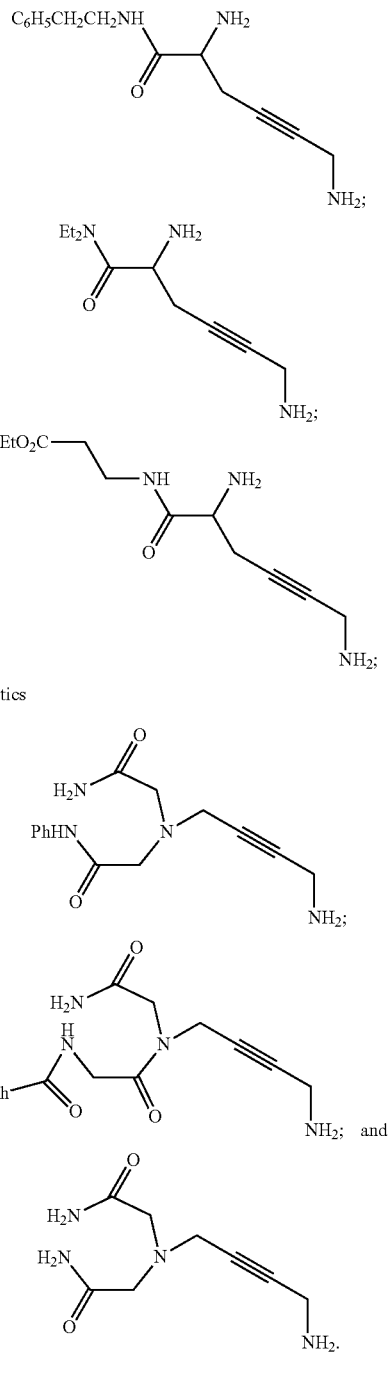

peptidomimetics

In accordance with another aspect, the therapeutic agent can comprise a β-haloamine, such as:

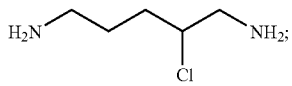

-continued

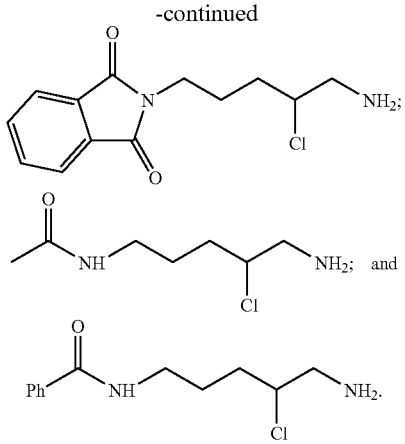

In accordance with yet another aspect, the therapeutic agent can comprise a $R_F$, $R_{Cl}$, and $R_3Si$ substituted amine such as:

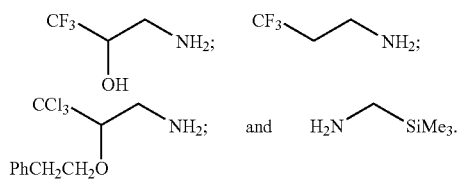

The therapeutic agents described above can be used for treatment of a disease or condition in a human where selective inhibition of amine oxidases, such as human TPQ-containing amine oxidases (AOC1, AOC2, and AOC3), human LTQ-containing amine oxidases (e.g., LOX, LOXL, LOXL2, LOX3, and LOXL4), as well as other human copper amine oxidases and non-mammalian copper amine oxidases, is beneficial. The present invention therefore provides a method of treating diseases by selectively inhibiting amine oxidase activity, which method comprises administering to an animal in need thereof a therapeutically effective amount of a therapeutic agent or compound in accordance with the present invention, wherein one or more compounds or therapeutic agents are administered in association with one or more non-toxic, pharmaceutically acceptable carriers and/or diluents and/or adjuvants and if desired other active ingredients.

The compounds or therapeutic agents in accordance with the present invention can be used to treat inflammatory conditions and diseases including but not limited to connective tissue inflammatory conditions and diseases such as ankylosing spondylitis, Reiter's syndrome, psoriatic arthritis, osteoarthritis or degenerative joint disease, rheumatoid arthritis, Sjogren's syndrome, Behget's syndrome, relapsing polychondritis, systemic lupus erythematosus, discoid lupus erythematosus, systemic sclerosis, eosinophilic fasciitis, polymyositis and dermatomyositis, polymyalgia rheumatica, vasculitis, temporal arteritis, polyarteritis nodosa, Wegener's granulomatosis, mixed connective tissue disease, and juvenile rheumatoid arthritis; gastrointestinal inflammatory conditions and diseases such as Crohn's disease, ulcerative colitis, irritable bowel syndrome (spastic colon), fibrotic conditions of the liver, inflammation of the oral mucosa (stomatitis), and recurrent aphtous stomatitis; central nervous system inflammatory conditions and diseases such as multiple sclerosis, Alzheimer's disease, and ischaemia-reperfusion injury associated with ischemic stroke; pulmonary inflammatory conditions and diseases such as asthma, chronic obstructive pulmonary disease, and adult respiratory distress syndrome; and skin inflammatory conditions and diseases such as contact dermatitis, atopic dermatitis, psoriasis, pityriasis rosea, lichen planus, and pityriasis rubra pilaris.

Moreover, the therapeutic agents of the invention can be used to treat diseases related to carbohydrate metabolism and complications thereof, such as diabetes and complications of diabetes including, but not limited to microvascular and macrovascular disease such as atherosclerosis, vascular retinopathies, retinopathy, nephropathy and nephrotic syndrome, neuropathies such as polyneuropathy, mononeuropathies, and autonomic neuropathy, and foot ulcers and joint problems, as well as increased risk of infection; diseases related to or caused by aberrations in adipocyte differentiation or function such as atherosclerosis and obesity; and vascular diseases such as atheromatous and nonatheromatous ateriosclerosis, ischemic heart disease including myocardial infarction, peripheral aterial occlusion, thromboangiitis obliterans (Buerger's disease), and Raynaud's disease and phenomenon.

In particular, the present compounds can be used to treat atherosclerosis. It is known that $AOC_3$ (HVAP-1) is expressed on adipocytes, smooth muscle cells, endothelial cells and is related to inflammation. Atherosclerotic plaque consists of accumulated intracellular and extracellular lipids, smooth muscle cells, connective tissue, and glycosaminoglycans. The earliest detectable lesion of atherosclerosis is the fatty streak (consisting of lipid-laden foam cells, which are macrophages that have migrated as monocytes from the circulation into the subendothelial layer of the intima), which later evolves into the fibrous plaque (consisting of intimal smooth muscle cells surrounded by connective tissue and intracellular and extracellular lipids).

The term "treat inflammation" is intended to include the administration of therapeutic agents of the present invention to a subject for purposes, which can include prophylaxis, amelioration, prevention or cure of an inflammatory condition or disease. Such treatment need not necessarily completely ameliorate the inflammatory condition or disease. Further, such treatment can be used in conjunction with other traditional treatments for reducing the inflammatory condition known to those of skill in the art.

In addition, as noted above, LOX is responsible for the lysine-derived cross-links in collagen and elastin, which is the essential step for biogenesis and repair of the fibrillar extracellular matrix. Despite what should be a harmful effect of lysyl oxidase inhibition early in life, there is growing evidence that the enzyme also plays a role in late-onset fibrotic conditions in man. Thus, selective inhibitors can be viewed as potential leads to development of anti-fibrotic chemotherapies.

Moreover, in addition to its essential role in connective tissue maturation, several new functions, as varied as tumor suppression, cellular senescence, developmental control, and cell motility (chemotaxis) have been described. Abnormal LOX activity contributes to a number of different diseases including atherosclerosis, aortic aneurysms, pulmonary fibrosis, and hepatic fibrosis. Also, LOX activity is increased in dementia, with LOX-positive plaques being particularly increased in Alzheimer's disease, suggesting that LOX in the extracellular matrix may be associated with plaque formation. Mammalian LOX has been shovel to translocate to the nuclei of smooth muscle cells and regulate chromatin structure and transcription. Selective inhibitors allow for crucial breakthroughs in identifying possible tissue-specific function of these enzymes.

Moreover, copper amine oxidases are ubiquitous in nature, and there is a possibility that certain bacterial or fungal CAOs may be crucial to their survival. Selective inhibitors of these enzymes can become therapeutic agents in man as anti-bacterial, anti-microbial, or anti-fungal agents.

The therapeutic agents can be provided in the form of pharmaceutical compositions. The pharmaceutical compositions of the present invention can be administered to any animal that can experience the beneficial effects of the compounds of the invention. Foremost among such animals are humans although the invention is not intended to be so limited.

The pharmaceutical compositions of the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route. Particularly preferred is oral administration. The dosage administered will be dependent upon the age, health, and weight of the recipient, kind of concurrent treatment, if any, frequency of treatment, and the nature of the effect desired.

In addition to the pharmacologically active compounds, the pharmaceutical preparations of the compounds can contain suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Slow-release and prolonged-release formulations may be used with particular excipients such as methacrylic acid—ethylacrylate copolymers, methacrylic acid—ethyl acrylate copolymers, methacrylic acid—methyl methacrylate copolymers and methacrylic acid—methyl methylacrylate copolymers. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The following examples provided are illustrative, but not limiting, of the method and compositions of the present invention. Other suitable modifications and adaptations of the variety of conditions and parameters normally encountered and obvious to those skilled in the art are within the spirit and scope of the invention.

EXAMPLES

In the following Examples, 0.9 mL aliquots of a solution of candidate inhibitor in 100 mM potassium phosphate buffer, pH 7.2 was mixed bovine plasma amine oxidase (0.1 mL, about 8 AM) and incubated at 30° C. aerobically. Aliquots (0.1 mL) were periodically withdrawn using disposable calibrated Drummond micropipettes and diluted with 1.0 mL of benzylamine (5 mM in 50 mM sodium phosphate buffer, pH 7.2) in a 1 cm quartz cuvette (1.5 mL volume). The rate of oxidation of benzylamine to benzaldehyde was measured by recording the increase in absorbance at 250 nm for 1 minute and compared to the rate of benzylamine oxidation in a companion control solution of enzyme without inhibitor. The concentration of active BPAO was estimated from the rate of benzylamine oxidation. Inhibitory potency values ($IC_{50}$ values) and partition values for inactivation of BPAO were measured at various times as in indicated in the Tables. $IC_{50}$ values for lysyl oxidase (LO), *arthrobacter globoformis* amine oxidase (AGAO) and *pichia pastoris* lysyl oxidase (PPLO) were also measured in a similar manner.

TABLE 1

Inactivation of BPAO by substituted allylamines and propargylamines

| Compound | | 20 min IC$_{50}$ (microM) | partition ratio |
|---|---|---|---|
| 1 | H$_2$N-CH$_2$-C≡C-CH$_2$-NHCH$_2$Ph | 1000 | 555 |
| 2 | H$_2$N-CH$_2$-C≡C-CH$_2$-NHCH$_2$CH$_2$Ph | 500 | 330 |
| 3 | H$_2$N-CH$_2$-C≡C-Ph | 700 | 461 |
| 4 | H$_2$N-CH$_2$-C≡C-Br | 10 | 6 |
| 5 | H$_2$N-CH$_2$-C≡C-CN | 13 | 10 |
| 6 | H$_2$N-CH$_2$-C≡C-CH$_2$-NH$_2$ | 20 | 20 |
| 7 | H$_2$N-CH$_2$-C≡C-C≡C-CH$_2$-NH$_2$ | 9 | 4.2 |
| 8 | H$_2$N-CH$_2$-CH=CH-CH$_2$-NH$_2$ | 2000 | — |
| 9 | H$_2$N-CH$_2$-CH=C(Cl)-CH$_2$-NH$_2$ | 24 | 29 |
| 10 | H$_2$N-CH$_2$-CH=CH-Cl (trans) | 2 | 2 |
| 11 | H$_2$N-CH$_2$-CH=CH-Cl (cis) | 11 | 6 |

TABLE 2

Inhibitory potency and partition ratios of homopropargylamine and its analogs on bovine plasma amine oxidase

| Compound | | IC$_{50}^{a}$ (μM) | Partition Ratio$^{b}$ |
|---|---|---|---|
| 1 | HC≡C-CH$_2$CH$_2$-NH$_2$ | 2.9 | $^{c}$ |
| 2 | H$_3$C-C≡C-CH$_2$CH$_2$-NH$_2$ | 10 | $^{c}$ |
| 3 | Ph-C≡C-CH$_2$CH$_2$-NH$_2$ | 13.5 | 13 |
| 4 | MeO-C$_6$H$_4$-C≡C-CH$_2$CH$_2$-NH$_2$ | 8.4 | 14 |
| 5 | O$_2$N-C$_6$H$_4$-C≡C-CH$_2$CH$_2$-NH$_2$ | $^{d}$ | N.D. |
| 6 | 3-pyridyl-C≡C-CH$_2$CH$_2$-NH$_2$ | 3.6 | 7 |
| 7 | Ph-CH$_2$-C≡C-CH$_2$CH$_2$-NH$_2$ | 4.6 | 8 |
| 8$^{e}$ | Ph-C≡C-CH(Ph)-CH$_2$-NH$_2$ | 108 | N.D. |
| 9$^{e}$ | HC≡C-CH$_2$-CH(Ph)-NH$_2$ | 6.5 mM | N.D. |

TABLE 2-continued

Inhibitory potency and partition ratios of homopropargylamine and its analogs on bovine plasma amine oxidase

| Compound | | $IC_{50}^a$ (μM) | Partition Ratio[b] |
|---|---|---|---|
| 10 | 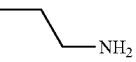 | 2.0 | 5 |

[a] The number listed represents the concentration needed to achieve 50% inactivation at the point (30 min) when the rapid phase of activity loss reaches the plateau point.
[b] N.D., partition ratio not determined.
[c] No apparent competing substrate activity
[d] The $IC_{50}$ cannot be determined because of the poor solubility of this compound. Enzyme lost 20% of activity at a concentration of 0.2 mM.
[e] Compound 8 and 9 were assayed as racemic mixtures.

TABLE 3

Additional analogs designed as potential selective lysyl oxidase (LO) inhibitors, Comparison of the inhibitory potency of lysine derivatives for bovine plasma amine oxidase (BPAO), LO, arthrobacter globiformis amine oxidase (AGAO), and pichia pastoris lysyl oxidase (PPLO)

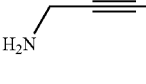

| | $IC_{50}$ (20 min) BPAO | $IC_{75}$ (20 min) LO* | $IC_{50}$ (BPAO)/$IC_{75}$(LO) | $IC_{50}$ (30 min) AGAO | $IC_{50}$ (30 min) PPLO |
|---|---|---|---|---|---|
| R = NHCH$_2$CH$_2$Ph | 1.8 mM | 0.45 mM | 1.11 | 0.25 mM | 0.25 mM |
| R = NHCH$_2$CONHCH$_2$COOEt | 0.09 mM | 0.65 mM | 0.14 | 3.5 mM | 3.0 mM |
| R = NEt$_2$ | 10 mM | 0.25 mM | 40 | 7 μM[#] | 5.0 mM |

*Assay performed by Amitha Palamakumbura and Philip Trackman, Boston University
[#] Determined on the basis of reversible competitive inhibition.

TABLE 4

| R = | 5 min $IC_{50}$ for BPAO |
|---|---|
| H | ~0.5 μM |
| CH$_3$CH$_2$ | ~0.5 μM |
| PhCH$_2$CH$_2$ | ~0.5 μM |
| Ph (R isomer) | 1.2 μM |
| Ph (S isomer) | 1.1 μM |

Having described the invention, the following is claimed:

1. A method of inhibiting quinone-dependent copper amine oxidases, comprising contacting the quinone dependent copper amine oxidase with an inhibitory amount of a alkylsilyl substituted propargylamines selected from the group consisting of:

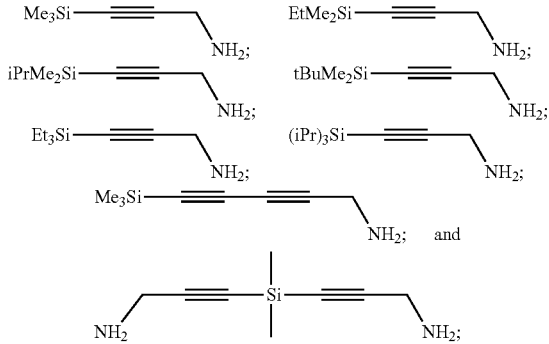

wherein Me is methyl, Et is ethyl, iPr is isopropyl, and tBu is tert-butyl.

* * * * *